United States Patent
Graf et al.

(10) Patent No.: US 6,274,759 B1
(45) Date of Patent: Aug. 14, 2001

(54) DIISOCYANATES CONTAINING HYDANTOIN GROUPS AND POLYURETHANES IN WHICH THEY ARE PRESENT

(75) Inventors: Hermann Graf, Mutterstadt; Udo Rotermund, Ortrand; Günter Mohrhardt, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/235,019

(22) Filed: Jan. 21, 1999

(30) Foreign Application Priority Data

Jan. 23, 1998 (DE) ................................ 198 02 547

(51) Int. Cl.⁷ .................................................. C07C 267/00
(52) U.S. Cl. .............................. 560/330; 528/45; 560/336
(58) Field of Search ............................. 528/45; 560/330, 560/336

(56) References Cited

U.S. PATENT DOCUMENTS 6,063,890 * 5/2000 Tye .......................................... 528/45

* cited by examiner

Primary Examiner—John M. Cooney, Jr.
(74) Attorney, Agent, or Firm—Fernando A. Borrego

(57) ABSTRACT

Diisocyanates of the formula (I)

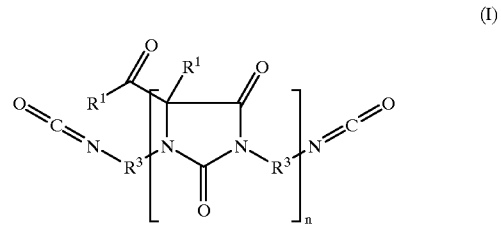

where $R^1$ is a $C_1$–$C_{10}$-hydrocarbon radical and $R^3$ is a $C_1$–$Cl_2$-hydrocarbon group and n is an integer from 1 to 10, are described.

6 Claims, No Drawings

DIISOCYANATES CONTAINING HYDANTOIN GROUPS AND POLYURETHANES IN WHICH THEY ARE PRESENT

The present invention relates to diisocyanates containing hydantoin groups, a process for their preparation, polyurethanes in which diisocyanates containing hydantoin groups are present and the use of these polyurethanes for producing fibers, films, foams, molding compositions, coatings and surface coating compositions as well as fibers, films, foams, molding compositions, coatings and surface coating compositions comprising such a polyurethane.

Polyurethanes are formed by reaction of polyisocyanates with polyols. Owing to the wide variety of possible reactions of the isocyanate group and its high reactivity, the polyisocyanates are used for producing foams, fibers, films, surface coating compositions and paints. For example, rigid polyurethane foams can be used for filling hollow spaces of refrigeration appliances or heating elements with foam since they have a low thermal conductivity. Selection of the raw materials enables the properties of the rigid foams to be varied within a wide range.

A summary overview of polyurethanes, their preparation and their use is described in Becker/Braun, Kunststoff Handbuch, Volume 7, Polyurethane, 3rd edition, 1993, Carl Hanser Verlag.

EP-A 0 744 419, 0 744 424, 0 744 425 and 0 744 427 disclose a process for synthesizing hydantoin-containing polyurethane prepolymers. All these processes have in common the fact that the hydantoin groups are formed in the prepolymer by a ring-closing condensation reaction which occurs at elevated temperatures. Furthermore, in this process, the hydantoin groups are only formed on prepolymers whose isocyanate groups are blocked by means of a protective group.

The protective group technique disclosed in these publications is disadvantageous, since it requires additional synthetic steps on the route to the finished polyurethane.

It is an object of the present invention to provide a process for synthesizing prepolymers and polyurethanes containing hydantoin groups and also corresponding prepolymers and polyurethanes, where the synthetic step for introducing and removing appropriate protective groups can be dispensed with. It is a further object of the present invention to provide a process for synthesizing prepolymers and polyurethanes containing hydantoin groups, in which process the prepolymer or polyurethane containing hydantoin groups is formed and a flame retardant is simultaneously formed, and also to provide the corresponding prepolymers and polyurethanes.

We have found that this object is achieved by a diisocyanate of the formula (I)

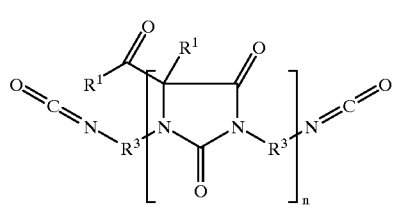

(I)

where $R^1$ is a $C_1$–$C_{10}$-hydrocarbon radical and $R^3$ is a $C_1$–$C_{12}$-hydrocarbon group and n is an integer from 1 to 10.

$R^1$ is preferably a $C_1$–$C_6$-alkyl radical, in particular a methyl, ethyl, propyl or butyl radical, or an aryl radical, particularly preferably a phenyl radical. $R^3$ is preferably an alkylene group having from 3 to 12 carbon atoms, a cycloalkylene group having from 3 to 12 carbon atoms or an arylene group having from 7 to 12 carbon atoms, in particular an unbranched alkylene group having from 4 to 8 carbon atoms, particularly preferably 6 carbon atoms, which at the ends is located next to the isocyanate group.

The object is also achieved by a process for preparing diisocyanates, in particular of the formula (I), in which phospholenes of the formula (II), where $R^1$ is as defined above and $R^2$ is a $C_1$–$C_{10}$-hydrocarbon group, are reacted with diisocyanates of the formula (III), where $R^3$ is as defined above, forming a phosphate of the formula (IV).

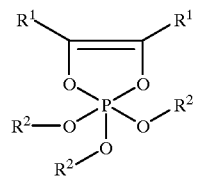

(II)

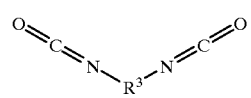

(III)

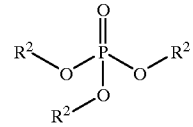

(IV)

Here, $R^1$ and $R^2$ can be identical or different.

Furthermore, it has surprisingly been found that both the diisocyanates of the formula (I) containing hydantoin groups and the polyurethanes obtained therefrom are significantly more thermally stable than the hydantoin-containing diisocyanates and polyurethanes described in the prior art.

As organic diisocyanates of the formula (III), it is possible to use all known suitable aliphatic, cycloaliphatic and aromatic compounds having more than one isocyanate group. Preferred organic diisocyanates are straight-chain or branched alkylene diisocyanates having from 1 to 12 carbon atoms, e.g. dodecane 1,12-diisocyanate, 2-ethylbutylene 1,4-diisocyanate, 2-methylpentylene 1,5-diisocyanate, butylene 1,4-diisocyanate, hexamethylene 1,6-diisocyanate (HDI); cycloaliphatic diisocyanates having from 3 to 12 carbon atoms, e.g. cyclohexyl 1,3-diisocyanate, cyclohexyl 1,4-diisocyanate, 1-isocyanato-3,3,5-trimethyl-5-isocyanatomethylcyclohexane (IPDI), hexahydrotolylene 2,4- and 2,6-diisocyanate and the corresponding isomer mixtures, dicyclohexylmethane 4,4'- , 2,2'- and 2,4'-diisocyanate and also the corresponding isomers mixtures and aromatic diisocyanates having from 7 to 12 carbon atoms, e.g. tolylene 2,4- and 2,6-diisocyanate (TDI) and their isomer mixtures, diphenylmethane 4,4'-, 2,2'- and 2,4'-diisocyanate (MDI) and also their isomer mixtures, mixtures of diphenylmethane 4,4'-, 2,2'-diisocyanates, polyphenylpolymethylene polyisocyanates (polymeric MDI), mixtures of diphenylmethane 4,4'-, 2,2'- and 2,4'-diisocyanates and polyphenylpolymethylene polyisocyanates (crude MDI) and mixtures of crude MDI and tolylene diisocyanates. Preference is given to using hexamethylene 1,6-diisocyanate (HDI), tolylene 2,4- and 2,6-diisocyanate (TDI) and their isomer mixtures, mixtures of diphenylmethane 4,4'-, 2,2'-diisocyanates (MDI) and polyphenylpolymethylene polyisocyanates (polymeric MDI).

In a further embodiment of the process of the present invention, the phosphate of the formula (IV) formed in the reaction is removed at least partially, preferably completely, from the reaction mixture.

Furthermore, in the reaction of the phospholenes of the formula (II) with the diisocyanates of the formula (III) in the process of the present invention, the diisocyanates of the formula (III) are preferably used in excess, particularly preferably at least in a two-fold excess.

This reaction forms a composition which comprises at least one diisocyanate of the formula (I), a diisocyanate of the formula (III) and possibly a phosphate of the formula (IV).

The amount of the flame-retardant phosphate of the formula (IV) present in the composition depends on the extent to which the phosphate of the formula (IV) has, as described above, been removed from the composition; the flame-retardant effect of the phosphate of the formula (IV) increases as the proportion present in the composition rises.

The proportion of the flame-retardant phosphate of the formula (IV) in the overall composition is selected such that the amount of phosphate of the formula (IV) present in the polyurethane formed as end product is sufficient to ensure a satisfactory flame-retardant effect.

The proportion of the phosphate of the formula (I) is from 0.1 to 25% by weight, preferably from 0.5 to 7% by weight, based on the total polyurethane and particularly preferably based on the A component of the polyurethane.

In addition, the viscosity of the composition can be controlled via the proportion of the phosphate of the formula (IV).

In a preferred embodiment of the invention, the ratios of (a) to (b) and to the diisocyanate of the formula (I) are from 1:1:1 to 6:1:1 and preferably from 1:1:1 to 4:1:1.

According to the present invention, particular preference is given to varying the viscosity of the not yet cured polyurethane or the polyurethane component by means of the phosphate of the formula (IV). This is particularly advantageous when the polyurethane is used for filling, preferably filling with foam, shapes having a complicated structure. The control of the viscosity in the direction of easy-flowing liquids is achieved by increasing the proportion of the phosphate of the formula (IV) in the not yet polymerized polyurethane or in the polyurethane components.

In a preferred embodiment, the proportion of the phosphate of the formula (IV) in all components used except for component (a) is from 0.5 to 30% by weight, preferably from 3 to 20% by weight.

The viscosity of the components used for the polyurethane synthesis, apart from component (a), is from 200 to 10,000 mPa·s, preferably from 600 to 3000 mPa·s, at 20° C.

Furthermore, according to the present invention, a polyurethane is obtainable from at least the constituents: at least one diisocyanate of the formula (I) or a composition comprising at least one diisocyanate of the formula (I), a diisocyanate of the formula (III) or a mixture thereof as organic polyisocyanate (a) and at least one diol as organic compound containing at least two reactive hydrogen atoms (b).

The constituent (b) is preferably an acrylate resin containing at least two hydroxyl groups per molecule and having a weight average molecular weight ($M_w$) of from 300 to 20,000 g/mol, preferably from 10,000 to 15,000 g/mol and particularly preferably from 2000 to 10,000 g/mol.

In the polyurethane of the present invention, the constituent (b) is preferably an acrylate resin, preferably if the urethane of the present invention is used as a readily curable surface coating composition.

Furthermore, it is preferred that not only the constituents (a) and (b) but also chain extenders and/or crosslinkers (c) or catalyst (d) or blowing agents (e) or flame retardants (f), auxiliaries and/or additives (g) or a mixture comprising at least two of these constituents are used in the process for producing the polyurethane of the present invention and are thus present in the polyurethane obtainable thereby.

In another embodiment of the process of the present invention, the polyurethane of the invention is prepared by reacting organic polyisocyanates (a) with organic compounds containing at least two reactive hydrogen atoms (b) and chain extenders and crosslinkers (c).

In an embodiment which is also preferred according to the present invention, the polyurethane of the present invention is prepared by reacting organic polyisocyanates (a) with organic compounds containing at least two reactive hydrogen atoms (b) and further catalysts (d).

In another embodiment of the process of the present invention for preparing the polyurethane of the present invention, organic polyisocyanates (a) are reacted with organic compounds containing at least two reactive hydrogen atoms (b) and chain extenders and crosslinkers (c) and catalysts (d).

A further embodiment of the process of the present invention for preparing polyurethanes is distinguished by the organic polyisocyanates (a) being reacted with the organic compounds containing at least two reactive hydrogen atoms (b) and blowing agents (e).

In a further embodiment of the process of the present invention, the organic polyisocyanates (a) are reacted with the organic compounds containing at least two reactive hydrogen atoms (b) and with chain extenders and crosslinkers (c) and also catalysts (d) for preparing the polyurethanes of the present invention.

In a further embodiment of the process of the present invention, the polyurethanes of the present invention are prepared by reacting organic polyisocyanates (a) with organic compounds containing at least two reactive hydrogen atoms (b) and also flame retardants (f).

In another embodiment of the process of the present invention, the polyurethanes of the present invention are prepared by reacting organic polyisocyanates (a) with organic compounds containing at least two reactive hydrogen atoms (b), chain extenders and crosslinkers (c) and flame retardants (f).

An embodiment of the process of the present invention is also constituted by the polyurethanes of the present invention being prepared by reacting organic polyisocyanates (a) with organic compounds containing at least two reactive hydrogen atoms (b) and auxiliaries and/or additives.

An additional embodiment of the process of the present invention is constituted by the polyurethane of the present invention being prepared by reacting organic polyisocyanates (a) with compounds containing at least two reactive hydrogen atoms (b) and chain extenders and/or crosslinkers (c) and also auxiliaries and/or additives (g).

In another embodiment of the process of the present invention, the polyurethane of the present invention is prepared by reacting organic polyisocyanates (a) with organic compounds containing at least two reactive hydrogen atoms (b) in the presence of catalysts (d) and blowing agents (e).

In another embodiment of the process of the present invention, the polyurethane of the present invention is prepared by reacting polyisocyanates (a) with organic compounds containing at least two reactive hydrogen atoms (b) and chain extenders and/or crosslinkers (c) in the presence of catalysts (d) and blowing agents (e).

In a further embodiment of the process of the present invention, the polyurethane of the present invention is prepared by reacting organic polyisocyanates (a) and compounds containing at least two reactive hydrogen atoms (b) and chain extenders and crosslinkers (c) in the presence of flame retardants (f) and blowing agents (e).

In another embodiment of the process of the present invention, the polyurethanes of the present invention are prepared by reacting organic polyisocyanates (a) with organic compounds containing at least two reactive hydrogen atoms (b) and, if desired, chain extenders and crosslinkers (c) in the presence of catalysts (d), blowing agents (e), flame retardants (f) and also, if desired, auxiliaries and/or additives (g).

All the above embodiments of the process of the present invention for preparing the polyurethanes of the present invention have in common the use of at least one diisocyanate of the formula (I). Furthermore, the component combinations of the above embodiments apply analogously to the polyurethanes and polyurethane compositions obtainable from these processes.

The preparation of the phospholene intermediates is described in Ramirez et al., Tetrahedrom 24, 1941, (1968).

In an embodiment which is preferred according to the present invention, the phospholenes are obtained by reacting a diketone containing the above-defined radicals $R^1$, where the two keto groups are preferably joined directly to one another, preferably diacetyl and benzil, with a phosphite whose oxygen atoms bear the above-described radicals $R^2$, preferably trimethyl phosphite, tripropyl phosphite, triphenyl phosphite and particularly preferably triethyl phosphite. The reaction is preferably carried out in a temperature range from $-20$ to $20°$ C., preferably from $-10$ to $10°$ C. and particularly preferably from 0 to $5°$ C. It is also preferred for the reaction to be carried out in an inert gas atmosphere, preferably in a nitrogen or argon atmosphere, or a mixture of both and particularly preferably in a nitrogen atmosphere. In the phospholene synthesis, it is also preferred according to the present invention for the product to be held at room temperature for a plurality of hours, preferably from 2 to 30 hours, more preferably from 10 to 20 hours and particularly preferably from 12 to 13 hours, after the reaction is complete. It has also been found to be advantageous to work up the resulting reaction product by distillation. Although the phospholene synthesis can be carried out in any suitable solvent, it has been found to be particularly advantageous to carry out the reaction without additional solvent.

The hydantoin-containing diisocyanates of the formula (I) are obtained by reacting a corresponding phospholene of the formula (II) with an isocyanate of the formula (III). The reaction is preferably carried out in a temperature range of from 0 to $80°$ C., preferably from 20 to $70°$ C. and particularly preferably from 30 to $50°$ C. Furthermore, it is advantageous in the process for preparing the hydantoin-containing diisocyanates of the formula (I) to carry out the reaction in a solvent, preferably an aprotic solvent, preferably selected so that its boiling point is within the abovementioned temperature ranges. Particular preference is given to aprotic polar and halogenated solvents, with the halogenated solvents being particularly preferred. Suitable halogenated solvents are, for example, carbon tetrachloride, trichloromethane, dichloromethane, monochloromethane, 1,2-dichloroethane, trichloroethylene and 1,1,1-trichloroethane, with dichloromethane being particularly preferred. Particular preference is given to carrying out the reaction in dichloromethane at a temperature at which the dichloromethane boils. Preference is also given to carrying out the reaction according to the present invention in an inert gas atmosphere, preferably an atmosphere of argon or nitrogen or a mixture thereof and particularly preferably of nitrogen. Preference is also given to both the phospholene of the formula (II) and the diisocyanate of the formula (III) being taken up in solvents. In addition, preference is given to the diisocyanate of the formula (III) being initially charged in a suitable solvent and the phospholene of the formula (II), likewise taken up in a solvent, being added to the solution of the diisocyanate of the formula (III) over a period of time. Furthermore, it is advantageous in the synthesis of the novel hydantoin-containing diisocyantes of the formula (I) for the reaction to be carried out by heating within the abovementioned temperature range until the component of which a deficiency is present has been completely reacted. After the reaction is complete, the solvent or solvents is/are preferably removed by distillation and the reaction product is likewise worked up by distillation, with a vacuum distillation, preferably in the range from 1 to 20 torr, being advantageous.

According to the present invention, preference is also given to mixing the hydantoin-containing diisocyanates of the formula (I) with further isocyanates such as polyisocyanates and diisocyanates, preferably diisocyanates, as are to be found in the listing of the polyisocyanates (a). However, particular preference is given to mixtures with diisocyanates referred to in the following as standard diisocyanates, with diarylalkyl diisocyanates, preferably diphenylmethane diisocyanate and particularly preferably diphenylmethane 4,4'-diisocyanate (MDI), and polymeric diarylalkyl diisocyanates, preferably diphenylmethane diisocyanate and particularly preferably diphenylmethane 4,4'-diisocyanate (polymeric MDI), being preferred.

According to the present invention, preference is given to using a mixture of a two-ring MDI with polymeric diisocyanates containing a higher number of rings. This mixture preferably has a viscosity in the range from 50 to 3000 mP·s, more preferably from 90 to 2500 mPa·s, at $25°$ C. Preference is also given to this mixture having an NCO content of 30–34% by weight. Furthermore, it is preferred according to the present invention that the monomeric MDI content is from 10 to 80 and preferably from 20 to 60% by volume of the total MDI mixture.

The novel hydantoin-containing diisocyanates of the formula (I), and also their mixtures with other isocyanates, can be used for preparing polyurethanes which can in turn be used for producing fibers, films, foams, molding compositions, coatings and surface coating compositions.

Particularly preferably, a rigid polyurethane foam is produced from at least one hydantoin-containing diisocyanate of the formula (I) or at least one of the abovementioned mixtures together with at least one polyol. The polyurethanes and in particular the rigid polyurethane foams are produced, after good mixing of the components, in a temperature range of from 10 to $70°$ C., preferably from 20 to $60°$ C., and particularly preferably from 35 to $55°$ C. The rigid polyurethane foams are particularly preferably produced in a mold which is configured as the negative of the rigid foam body resulting from polyurethane formation. The moldings obtained from the rigid polyurethane foams preferably have a density of from 50 to 90 $kg/m^3$, preferably from 60 to 80 $kg/m^3$ and particularly preferably from 65 to 75 $kg/m^3$. The time to removal from the mold is preferably from 10 to 60 minutes, more preferably from 20 to 40 minutes and particularly preferably from 25 to 35 minutes.

The novel hydantoin-containing diisocyanate of the formula (I), in particular the diisocyanates of the formula (I) in which the radical $R^3$ is a $C_1$–$Cl_2$-, preferably $C_4$–$C_8$- and particularly preferably $C_5$–$C_6$-alkylene which is preferably unbranched, can be reacted with appropriate hydroxyl-containing acrylate resins to produce surface coating compositions. A hydantoin-containing diisocyanate of the formula (I) which is derived from hexamethylene 1,6-diisocyanate as diisocyanate of the formula (III) has been found to be particularly useful for the synthesis of surface coating compositions. Suitable hydroxyl-containing acrylate resins are, in particular, those having a weight average molecular weight in a range from 2000 to 20,000 g/mol, preferably from 3000 to 10,000 g/mol and particularly preferably from 5000 to 7000 g/mol. Furthermore, the suitable acrylate resins preferably have an OH number in the range from 50 to 200, more preferably from 70 to 150 and particularly preferably from 80 to 140.

Pigments, preferably $TiO_2$ as white pigment, can be used in the polyurethanes, rigid polyurethane foams and polyurethane-based surface coating compositions of the present invention, preferably the polyurethane-based surface coating composition.

The novel diisocyanate of the formula (I) also has the effect of making the polyisocyanate component (a) comprising it more fluid than one without it. For this reason, preferably in the case of surface coating compositions, preferably those comprising a hydroxyl-containing acrylate resin, which have as one constituent a mixture of the diisocyanate of the formula (I) and the component (a), the same viscosity can be achieved using a smaller amount of solvent than is possible without the diisocyanate of the formula (I). Furthermore, the presence of the diisocyanate of the formula (1) enables the elasticity of the abovementioned surface coating compositions to be improved relative to comparable surface coating compositions made up of conventional constituents.

The constituents or components (a) to (g) are described by way of example below.

Polyisocyanates (a)

Organic polyisocyanates used are preferably the aliphatic, cycloaliphatic and particularly preferably aromatic polyfunctional isocyanates known per se. In one embodiment of the present invention, particular preference is given to polyisocyanates containing two isocyanate groups if such polyisocyanates are not to have a crosslinking action. However, if a crosslinking action of the polyisocyanates is preferred, polyisocyanates containing more than two isocyanate groups are employed in another embodiment of the present invention.

Particularly preferred organic polyisocyanates (a) are, for example, alkylene diisocyanates having from 4 to 12 carbon atoms in the alkylene radical, e.g. dodecane 1,12-diisocyanate, 2-ethyltetramethylene 1,4-diisocyanate, 2-methylpentamethylene 1,5-diisocyanate, tetramethylene 1,4-diisocyanate and preferably hexamethylene 1,6-diisocyanate; cycloaliphatic diisocyanates such as cyclohexane 1,3- and 1,4-diisocyanate and also any mixtures of these isomers, 1-isocyanato-3,3,5-trimethyl-5-isocyanatomethylcyclohexane (IPDI), hexahydrotolylene 2,4- and 2,6-diisocyanate and also the corresponding isomer mixtures, dicyclohexylmethane 4,4'-, 2,2'- and 2,4'-diisocyanate and also the corresponding isomer mixtures, and preferably aromatic diisocyanates and polyisocyanates such as tolylene 2,4- and 2,6-diisocyanate and the corresponding isomer mixtures, diphenylmethane 4,4'-, 2,4'- and 2,2'-diisocyanate and the corresponding isomer mixtures, mixtures of diphenylmethane 4,4'- and 2,2'-diisocyanates, polyphenylpolymethylene polyisocyanates, mixtures of diphenylmethane 4,4'-, 2,4'- and 2,2'-diisocyanates and polyphenylpolymethylene polyisocyanates, for example crude MDI, and mixtures of crude MDI and tolylene diisocyanates. The organic diisocyanates and polyisocyanates can be used individually or in the form of mixtures.

As organic polyisocyanates (a), use is frequently also made of modified polyfunctional isocyanates, i.e. products which are obtained by chemical reaction of organic diisocyanates and/or polyisocyanates. Examples of isocyanates of this type are diisocyanates and/or polyisocyanates containing ester, urea, biuret, carbodiimide, isocyanurate and/or urethane groups. Specific examples are: organic, preferably aromatic polyisocyanates containing urethane groups and having an NCO content of from 33.6 to 15% by weight, preferably from 31 to 21% by weight, based on the total weight; for example diphenylmethane 4,4'-diisocyanate modified with low molecular weight diols, triols, dialkylene glycols, trialkylene glycols or polyoxyalkylene glycols having molecular weights of up to 6000, in particular up to 1500, modified diphenylmethane 4,4'-diisocyanate, modified diphenylmethane 4,4'- and 2,4'-diisocyanate mixtures or modified crude MDI, with the dialkylene or polyoxyalkylene glycols being able to be used individually or as mixtures. Examples which may be mentioned are: diethylene glycol, dipropylene glycol, polyoxyethylene, polyoxypropylene and polyoxypropylene-polyoxyethylene diols, triols and/or tetrols. According to the present invention, preference is also given to prepolymers containing NCO groups, having NCO contents of from 25 to 3.5% by weight, preferably from 21 to 14% by weight, based on the total weight of the prepolymer, and prepared from the polyester polyols and/or preferably polyether polyols described below and diphenylmethane 4,4'-diisocyanate, mixtures of diphenylmethane 2,4'- and 4,4'-diisocyanate, tolylene 2,4- and/or 2,6-diisocyanates or crude MDI. Also preferred are liquid polyisocyanates containing carbodiimide groups and/or isocyanurate rings and having an NCO content of from 33.6 to 15% by weight, preferably from 31 to 21% by weight, based on the total weight of the polyurethane, for example those based on diphenylmethane 4,4'-, 2,4'- and/or 2,2'-diisocyanate and/or tolylene 2,4- and/or 2,6-diisocyanate.

The modified polyisocyanates can be mixed with one another or with unmodified organic polyisocyanates, for example diphenylmethane 2,4'- and/or 4,4'-diisocyanate, crude MDI, tolylene 2,4- and/or 2,6-diisocyanate.

Particular preference is given to the following organic polyisocyanates which have been found to be particularly useful in the preparation of cellular elastomers:

Prepolymers containing NCO groups and having an NCO content of from 25 to 9% by weight, based on the prepolymer, in particular those based on polyether polyols or polyester polyols and one or more diphenylmethane diisocyanate isomers, advantageously diphenylmethane 4,4'-diisocyanate, and/or modified organic polyisocyanates containing urethane groups and having an NCO content of from 33.6 to 15% by weight, in particular those based on diphenylmethane 4,4'-diisocyanate or diphenylmethane diisocyanate isomer mixtures.

To produce flexible polyurethane foams as a subgroup of the cellular elastomers, the following have been found to be useful:

Mixtures of tolylene 2,4- and 2,6-diisocyanates, mixtures of tolylene diisocyanates and polyphenylpolymethylene polyisocyanate or, in particular, mixtures of the abovementioned prepolymers based on diphenylmethane diisocyanate isomers and crude MDI, preferably polyphenylpolymethylene polyisocyanate having a diphenylmethane diisocyanate isomer content of from 30 to 80% by weight.

Compounds Containing at Least two Reactive Hydrogens (b)

As organic compounds containing at least two reactive hydrogens (b), preference is given to using the compounds described in more detail above, if desired in admixture with further compounds having a functionality of from 2 to 8, preferably from 2 to 4, and a molecular weight of from 300 to 10,000, preferably from 1000 to 6000. Particular preference is given to, for example, polyetherpolyamines and/or preferably polyols selected from the group consisting of polyether polyols, polyester polyols, polythioether polyols, polyesteramides, hydroxyl-containing polyacetals and hydroxyl-containing aliphatic polycarbonates or mxitures of at least two of the polyols mentioned. Polyester polyols and/or polyether polyols are preferably employed.

Suitable polyester polyols can be prepared, for example, from organic dicarboxylic acids having from 2 to 12 carbon atoms, preferably aliphatic dicarboxylic acids having from 4 to 6 carbon atoms, and polyhydric alcohols, preferably diols, having from 2 to 12 carbon atoms, preferably from 2 to 6 carbon atoms. Preferred dicarboxylic acids are: succinic acid, glutaric acid, adipic acid, suberic acid, azelaic acid, sebacic acid, decanedicarboxylic acid, maleic acid, fumaric acid, phthalic acid, isophthalic acid and terephthalic acid. The dicarboxylic acids can be used either individually or as mixtures. In place of the free dicarboxylic acids, it is also possible to use the corresponding dicarboxylic acid derivatives, for example dicarboxylic esters of alcohols having from 1 to 4 carbon atoms or dicarboxylic anhydrides. Preference is given to using dicarboxylic acid mixtures of succinic, glutaric and adipic acid and in particular adipic acid. Examples of dihydric and polyhydric alcohols, in particular diols, are: ethanediol, diethylene glycol, 1,2- or 1,3-propanediol, dipropylene glycol, 1,4-butanediol, 1,5- pentanediol, 1,6-hexanediol, 1,10-decanediol, glycerol and trimethylolpropane. Preference is given to using ethanediol, diethylene glycol, 1,4-butanediol, 1,5-pentanediol and 1,6-hexanediol. In the process of the present invention for preparing the polyurethanes, it is also possible to use: polyester polyols derived from lactones, for example ε-caprolactone, or hydroxycarboxylic acids, for example ω-hydroxycaproic acid.

To prepare the polyester polyols, the organic, for example aromatic and preferably aliphatic, polycarboxylic acids and/ or derivatives and polyhydric alcohols can be polycondensed in the absence of catalysts or preferably in the presence of esterification catalysts. The polycondensation is preferably carried out in an atmosphere of inert gas, for example nitrogen, carbon monoxide, helium, argon and others, in the melt at from 150 to 200° C., preferably from 180 to 220° C., at atmospheric pressure or under reduced pressure, to a desired acid number. The resulting acid number is advantageously <10, preferably <2. According to a preferred embodiment, the esterification mixture is polycondensed at the abovementioned temperatures to an acid number of from 80 to 30, preferably from 40 to 30, under atmospheric pressure and subsequently under a pressure of <500 mbar, preferably from 50 to 150 mbar. Suitable esterification catalysts are, for example, iron, cadmium, cobalt, lead, zinc, antimony, magnesium, titanium and tin catalysts in the form of metals, metal oxides or metal salts.

The polycondensation can, however, also be carried out in the presence of diluents and/or entrainers, for example benzene, toluene, xylene or chlorobenzene, to azeotropically distill off the water of condensation. To prepare the polyester polyols, the organic polycarboxylic acids and/or derivatives and polyhydric alcohols are advantageously polycondensed in a molar ratio of 1:1–1.8, preferably 1:1.05–1.2.

The polyester polyols obtained preferably have a functionality of from 2 to 4, in particular from 2 to 3, and a molecular weight of from 480 to 3000, preferably from 1000 to 3000.

However, polyols used are preferably polyether polyols which are prepared by known methods, for example by anionic polymerization using alkali metal hydroxides such as sodium or potassium hydroxide or alkali metal alkoxides such as sodium methoxide, sodium or potassium ethoxide or potassium isopropoxide as catalysts with addition of at least one initiator molecule containing from 2 to 8, preferably from 2 to 4, reactive hydrogen atoms in bound form.

They can also be prepared from one or more alkylene oxides having alkylene radicals containing from 2 to 4 carbon atoms by cationic polymerization using Lewis acids such as antimony pentachloride, boron fluoride etherate, etc., or bleaching earth as catalyst.

Examples of suitable alkylene oxides are 1,3-propylene oxide, 1,2- or 2,3-butylene oxide, styrene oxide, THF and preferably ethylene oxide and 1,2-propylene oxide. The alkylene oxides can be used individually, alternately in succession or as mixtures.

Suitable initiator molecules are, for example: water, organic dicarboxylic acids such as succinic acid, adipic acid, phthalic acid and terephthalic acid, aliphatic and aromatic, unalkylated, N-monoalkylated, N,N- and N,N'-dialkylated diamines having from 1 to 2 carbon atoms in the alkyl radical, for example unalkylated, monoalkylated and dialkylated ethylenediarnine, diethylenetriamine, triethylenetetramine, 1,3-propylenediamine, 1,3- or 1,4- butylenediamine, 1,2-, 1,3-, 1,4-, 1,5- and 1,6- hexamethylenediamine, phenylenediamine, 2,3-, 2,4- and 2,6-tolylenediamine and 4,4'-, 2,4'- and 2,2'- diaminodiphenylmethane.

Further preferred initiator molecules are: alkanolamines such as ethanolamine, N-methylethanolamine and N-ethylethanolamine, dialkanolamines such as diethanolamine, N-methyldiethanolamine and N-ethyldiethanolamine and trialkanolamines such as triethanolamine, and ammonia. Preference is given to using polyhydric, in particular dihydric and/or trihydric alcohols such as ethanediol, 1,2- and 2,3-propanediol, diethylene glycol, dipropylene glycol, 1,4-butanediol, 1,6-hexanediol, glycerol, trimethylolpropane and pentaerythritol or sugars, preferably beet sugar.

The polyether polyols, preferably polyoxypropylene polyols and polyoxypropylene-polyoxyethylene polyols, have a functionality of preferably from 2 to 8 and a molecular weight of from 300 to 10,000, preferably from 1000 to 6000 and particularly preferably from 1500 to 5000. Suitable polyoxytetramethylene glycols have a molecular weight up to about 3500.

Further polyether polyols which are useful are, in particular, polymer-modified polyether polyols, preferably graft polyether polyols, in particular those based on styrene and/or acrylonitrile. These can be prepared by in situ polymerization of acrylonitrile, styrene or preferably mixtures of styrene and acrylonitrile, for example in a weight ratio of from 90:10 to 10:90, preferably from 70:30 to 30:70, advantageously using the abovementioned polyether polyols as described in the German Patents 11 11 349, 12 22 669 (U.S. Pat. Nos. 3,304,273, 3,383,351, 3,523,039), 1 152 536 (GB 1 040 452) and 1 152 537 (GB 9 876 618). Also suitable are polyether polyol dispersions comprising as dispersant phases, usually in an amount of from 1 to 50% by weight, preferably from 2 to 25% by weight, e.g. polyureas, polyhydrazides, polyurethanes containing bound tert-amino groups and/or melamine. Such dispersions are described, for example, in EP-B-011 752 (U.S. Pat. No. 4,304,708), U.S. Pat. No. 4,374,209 and DE-A-32 31 497.

Like the polyester polyols, the polyether polyols can be used individually or in the form of mixtures. They may also be mixed with the graft polyether polyols or polyester polyols or with the hydroxyl-containing polyester amides, polyacetals, polycarbonates and/or polyetherpolyamines.

Suitable hydroxyl-containing polyacetals are, for example, the compounds which can be prepared from glycols such as diethylene glycol, triethylene glycol, bis(4-hydroxyethylphenyl)dimethylmethane or hexanediol and formaldehyde. Suitable polyacetals can also be prepared by polymerization of cyclic acetals.

Suitable hydroxyl-containing polycarbonates are, in particular, ones which can be prepared, for example, by reacting diols such as 1,3-propanediol, 1,4-butanediol and/or 1,6-hexanediol, diethylene glycol, triethylene glycol or tetraethylene glycol with diaryl carbonates, for example diphenyl carbonate, or phosgene.

The preferred polyester amides include, for example, the predominantly linear condensates obtained from polybasic, saturated and/or unsaturated carboxylic acids, for example their anhydrides, or polyfunctional saturated and/or unsaturated aminoalcohols or mixtures of polyfunctional alcohols and aminoalcohols and/or polyamines.

Preferred polyetherpolyamines which are suitable according to the present invention can be prepared from the abovementioned polyether polyols by known methods. Examples which may be mentioned are the cyanoalkylation of polyoxyalkylene polyols and subsequent hydrogenation of the nitrile formed (U.S. Pat. No. 3,267,050) or the partial or complete amination of polyoxyalkylene polyols using amines or ammonia in the presence of hydrogen and catalysts (DE 12 15 373).

According to the present invention, particular preference is given to 2- to 3-functional polyetherols made up of propylene oxide and ethylene oxide in which preferably from 10 to 50% by weight, more preferably from 15 to 30% by weight and particularly preferably from 20 to 25% by weight, of ethylene oxide units are incorporated and which, in addition, have an OH number in the range from 10 to 50, preferably from 15 to 40 and particularly preferably from 20 to 30.

Chain Extenders and/or Crosslinkers (c)

The polyurethanes can be prepared with or without the use of chain extenders and/or crosslinkers. However, the addition of chain extenders, crosslinkers or, if desired, mixtures thereof can prove to be advantageous for modifying the mechanical properties, for example the hardness. The chain extenders or crosslinkers are, insofar as they possess at least two reactive hydrogen atoms, a subgroup of the compounds containing at least two reactive hydrogens (component (a)).

Chain extenders and/or crosslinkers used are diols and/or triols having molecular weights of <400, preferably from 60 to <300.

Examples of suitable chain extenders/crosslinkers are aliphatic, cycloaliphatic and/or araliphatic diols having from 2 to 14, preferably from 2 to 10, carbon atoms, for example ethylene glycol, 1,3-propanediol, 1,10-decanediol, o-, m-, p-dihydroxycyclohexane, diethylene glycol, dipropylene glycol and preferably 1,4-butanediol, 1,6-hexanediol and bis(2-hydroxyethyl)hydroquinone, triols such as 1,2,3-trihydroxycyclohexane, glycerol and trimethylolpropane and low molecular weight hydroxyl-containing polyalkylene oxides based on ethylene oxide and/or 1,2-propylene oxide and the abovementioned diols and/or triols as initiator molecules.

To produce cellular elastomer moldings and integral foams, secondary aromatic diamines, 3,3'-dialkyl- and/or 3,3', 5,5'-tetralkyl-substituted diamino-diphenylmethanes can also be employed instead of or in admixture with the abovementioned diols and/or triols as chain extenders and/or crosslinkers (b).

Preferred secondary aromatic diamines are: N,N'-dialkyl-substituted aromatic diamines having from 1 to 20, preferably from 1 to 4, carbon atoms in the N-alkyl radical, e.g. N,N'-di-sec-phenyl-, N,N'-di-sec-hexyl-, N,N'-di-sec-decyl-, N,N'-dicyclohexyl-p- or -m-phenylenediamine, N,N'-dimethyl-, N,N'-diethyl-, N,N'-diisopropyl-, N,N'-di-sec-butyl-, N,N'-dicyclohexyl-4,4'-diaminodiphenylmethane and N,N'-di-sec-butylbenzidine. These can, if desired, be substituted by alkyl radicals on the aromatic ring.

Catalyst (d)

As catalyst (d) for preparing polyurethanes, use is made, in particular, of compounds which strongly accelerate the reaction of the compounds containing reactive hydrogen atoms, in particular hydroxyl groups, of the component (b) and, if used, (c) with the organic, modified or unmodified polyisocyanates (a). Suitable catalysts are organic metal compounds, preferably organic tin compounds such as tin (II) salts of organic carboxylic acids, for example tin(II) acetate, tin(II) octoate, tin(II) ethylhexanoate and tin(II) laurate, and the dialkyltin(IV) salts of organic carboxylic acids, for example dibutyltin diacetate, dibutyl dilaurate, dibutyltin maleate and dialkyltin diacetate. The organic metal compounds are used alone or preferably in combination with strongly basic amines. Examples which may be mentioned are amidines such as 2,3-dimethyl-3,4,5,6-tetrahydro-pyrimidine, tertiary amines such as triethylamine, tributylamine, dimethylbenzylamine, N-methylmorpholine, N-ethylmorpholine, N-cyclohexylmorpholine, N,N,N',N'-tetramethylethylenediamine, N,N,N',N,-tetramethyl-butanediamine, N,N,N',N'-tetramethylhexane- 1,6-diamine, pentamethyldiethylenetriamine, bis(dimethyl-aminoethyl) ether, bis(dimethylaminopropyl)urea, dimethylpiperazine, 1,2-dimethylimidazole, 1-azabi-cyclo[3.3.0]octane and preferably 1,4-diaza-bicyclo[2.2.2]octane, and alkanolamine compounds such as triethanolamine, triisopropanolamine, N-methyl-diethanolamine and N-ethyldiethanolamine and dimethylethanolamine.

Further preferred catalysts are: tris(dialkylaminoalkyl)-s-hexahydrotriazines, in particular tris(N,N-dimethylaminopropyl)-s-hexahydrotriazine, tetraalkylammonium hydroxides such as tetramethylammonium hydroxide, alkali metal hydroxides such as sodium hydroxide and alkali metal alkoxides such as sodium methoxide and potassium isopropoxide and also alkali metal salts of long-chain fatty acids having from 10 to 20 carbon atoms and possible lateral OH groups. Preference is given to using from 0.001 to 5% by weight, in particular from 0.05 to 2% by weight, of catalyst or catalyst combination, based on the weight of the component (b).

Blowing Agents (e)

To produce polyurethane foams, water is used as chemical blowing agent (e); the water reacts with isocyanate groups to form amine groups and carbon dioxide, the actual blowing gas. The amounts of water which are advantageously used are from 0.1 to 5 parts by weight, preferably from 1.5 to 3.5 parts by weight and particularly preferably from 2.0 to 3.0 parts by weight, based on 100 parts by weight of the polyhydroxy compound (b), or mixtures of organic compounds containing at least two reactive hydrogen atoms, preferably relatively high molecular weight polyhydroxy compounds (b) with chain extenders and/or crosslinkers (c).

In admixture with water, physically acting blowing agents can also be used as blowing agent (e). Suitable physically acting blowing agents are, in particular, liquids which are inert toward the organic, modified or unmodified polyisocyanates (a) and have a boiling point of less than 100° C., preferably less than 50° C. and particularly preferably from −50 to 30° C., at atmospheric pressure, so that they vaporize under the action of the exothermic polyaddition reaction. Examples of such liquids are hydrocarbons such as isopentane, preferably industrial mixtures of n- and isopentane, n- and iso-butane, n- and iso-propane, cycloalkanes such as cyclohexane and cyclopentane, ethers such as furan, dimethyl ether and diethyl ether, ketones such as acetone and methyl ethyl ketone, alcohol carboxylates such as methyl formate, dimethyl oxalate and ethyl acetate and halogenated hydrocarbons such as methylene chloride, dichloromonofluoromethane, difluoromethane, difluorochloromethane, trifluoromethane, difluoroethane, tetrafluoroethane, heptafluoropropane, 1-chloro-2,2-difluoroethane, 1-chloro-1,1-difluoroethane and 1-chloro-1,2-difluoroethane. It is also possible to use mixtures of these low-boiling liquids, for example of difluoromethane and 1-chloro-1,1-difluoroethane and/or with other halogen-substituted or unsubstituted hydrocarbons. Another blowing agent which is preferred according to the present invention is $CO_2$, either alone or in admixture with other blowing agents, preferably water.

The amount of physically acting blowing agents can be determined in a simple manner as a function of the desired foam density and is from 0 to 25 parts by weight, preferably from 1 to 25 parts by weight and particularly preferably from 2 to 15 parts by weight, per 100 parts by weight of the polyhydroxyl compounds (b). It may be advantageous to mix the modified or unmodified polyisocyanates (a) with the inert, physically acting blowing agent and thereby reduce the viscosity.

Flame Retardants (f)

Suitable flame retardants (f) apart from the phosphate of the formula (IV) are, for example, tricresyl phosphate, tris(2-chloroethyl) phosphate, tris(2-chloropropyl) phosphate, tetrakis(2-chloroethyl) ethylene diphosphate, dimethyl methanephosphonate, diethyl diethanolaminomethylphosphonate and also commercial halogenated flame-retardant polyols.

In general, it has been found to be advantageous to use from 5 to 50 parts by weight, preferably from 5 to 25 parts by weight, of the flame retardants mentioned per 100 parts by weight of the components (a) to (e).

Further information on the abovementioned other customary auxiliaries and additives may be found in the specialist literature, for example in the monograph by J. H. Saunders and K. C. Frisch *"High Polymers"*, Volume XVI, *Polyurethanes*, part 1 and part 2, Interscience Publishers, 1962 and 1964, or the *Kunstoff-Handbuch, Polyurethane*, Volume VII, Hanser-Verlag, Munich/Vienna, 1st and 2nd Editions, 1966 and 1983.

To prepare the polyurethanes of the present invention, the organic polyisocyanates (a), the organic compounds containing at least two reactive hydrogen atoms (b) and, if desired, chain extenders and/or crosslinkers (c) are reacted in such amounts that the equivalence ratio of the NCO groups of the polyisocyanates (a) to the sum of the reactive hydrogen atoms of the component (b) and, if used, (c) and, when using water as blowing agent, also the water is 0.85–1.25:1, preferably 0.95–1.15:1 and in particular 1.05:1. If the polyurethanes contain at least some bound isocyanurate groups, it is usual to employ a ratio of NCO groups of the polyisocyanates (a) to the sum of the reactive hydrogen atoms of the component (b) and, if used, (c) of 1.5–20:1, preferably 1.5–8:1.

Auxiliaries and/or Additives (g)

If desired, auxiliaries and/or additives (g) can be incorporated into the reaction mixture for producing moldings having a compacted surface zone and a cellular core. Examples which may be mentioned are surface-active substances, foam stabilizers, cell regulators, fillers, dyes, pigments, if desired flame retardants, hydrolysis inhibitors, fungistatic and bacteriostatic substances. Examples of suitable surface-active substances are compounds which serve to aid the homogenization of the starting materials and may also be suitable for regulating the cell structure of the base materials. Preferred surface-acting substances are, for example, emulsifiers such as the sodium salt of castor oil sulfates or of fatty acids and also amine salts of fatty acids, for example diethylamine oleate, diethanolamine stearate, diethanolamine ricinoleate, salts of sulfonic acids, e.g. alkali metal or ammonium salts of dodecylbenzene- or dinaphthylmethanedisulfonic acid or ricinoleic acid; foam stabilizers such as siloxane-oxyalkylene copolymers and other organopolysiloxanes, ethoxylated alkylphenols, ethoxylated fatty alcohols, paraffin oils, castor oil or ricinoleic esters, Turkey red oil, peanut oil and cell regulators such as paraffins, fatty alcohols, dimethylpolysiloxanes. Oligomeric acrylates having polyoxyalkylene and fluoroalkane radicals as side groups are also suitable for improving the emulsifying action, the cell structure and/or stabilizing the foam. The surface-active substances are usually employed in amounts of from 0.01 to 5 parts by weight, based on 100 parts by weight of the components (b) to (f).

Preferred mold release agents are: reaction products of fatty acid esters with polyisocyanates, salts of polysiloxanes containing amino groups and fatty acids, salts of saturated or unsaturated (cyclo)aliphatic carboxylic acids having at least 8 carbon atoms and tertiary amines and also, in particular, internal mold release agents such as carboxylic esters and/or carboxamides, as described in EP-A-153 639 or DE-A-36 07 447.

For the purposes of the present invention, fillers, in particular reinforcing fillers, are the customary organic and inorganic fillers, reinforcing materials, weighting agents, agents for improving the abrasion behavior in paints, coating compositions, etc. known per se.

Specific Preferred Examples are:

Inorganic fillers such as siliceous minerals, for example sheet silicates such as antigorite, serpentine, hornblendes, amphiboles, chrysotile, talc; metal oxides such as kaolin, aluminum oxides, titanium oxides and iron oxides, metal salts such as chalk, barite and inorganic pigments such as cadmium sulfide, zinc sulfide, and also glass, etc. Preference is given to using kaolin (China clay), aluminum silicate and coprecipitants of barium sulfate and aluminum silicate and also natural and synthetic fibrous minerals such as wollastonite, metal fibers and in particular glass fibers of various lengths which may, if desired, be coated with a size. Examples of organic fillers are carbon, melamine, rosin, cyclopentadienyl resins and graft polymers and also cellulose fibers, polyamide, polyacrylonitrile, polyurethane and polyester foams and organic fillers based on aromatic and/or aliphatic dicarboxylic esters and, in particular, carbon fibers.

The inorganic or organic fillers can be used individually or as mixtures and are advantageously incorporated into the reaction mixture in amounts of from 0.5 to 50% by weight, preferably from 1 to 40% by weight, based on the weight of the components (for example (b) to (f)).

The invention is illustrated by the non-limiting examples below.

EXAMPLES

I. Phospholenes

The general procedure is to react freshly distilled diacetyl or benzil dropwise with a phosphite at 0–5° C. under a nitrogen atmosphere. The mixture is held at 20° C. for a number of hours and is subsequently distilled under reduced pressure.

The reaction of diacetyl with trimethyl phosphite gives 2,2,2-trimethoxy-4,5-dimethyl-2,2-dihydro-1,3,2-dioxaphospholene which has a boiling point of 62° C. at 3 mbar and an index of refraction of $n^{20}_D$- 1.4398.

The reaction of benzil with trimethyl phosphite gives 2,2,2-trimethoxy-4,5-diphenyl-2,2-dihydro-1,3,2-dioxaphospholene.

The reaction of diacetyl with triphenyl phosphite gives 2,2,2-triphenoxy-4,5-diphenyl-2,2-dihydro-1,3,2-dioxaphospholene.

The reaction of benzil with triphenyl phosphite gives 2,2,2-triphenoxy-4,5-diphenyl-2,2-dihydro-1,3,2-dioxaphospholene.

The reaction of diacetyl with triethyl phosphite gives 2,2,2-triethoxy-4,5-dimethyl-2,2-dihydro-1,3,2-dioxaphospholene which has a boiling point of 58° C. at 2 mbar and an index of refraction of $n^{22}_D$=1.4383.

II. Diisocyanates Containing Hydantoin Groups 431 g (2.48 mol) of tolylene 2,4-diisocyanate (2,4-TDI) and 200 ml of dry dichloromethane were placed in a reaction vessel and, at room temperature under inert gas, a solution of 46 g (0.219 mol) of 2,2,2-trimethoxy-4,5-dimethyl-2,2-dihydro-1,3,2-dioxaphospholine in 100 ml of dichloromethane was added dropwise. The mixture was refluxed for 24 hours and the solvent was subsequently distilled off under atmospheric pressure. Excess 2,4-TDI and the reaction by-product trimethyl phosphate were distilled off under reduced pressure. The distillation residue is the reaction product 5-acetyl-1,3-bis(3-isocyanato-4-methylphenyl)-5-methyl-hydantoin and is a yellow, viscous oil which gradually solidifies to give a solid having a melting point of >320° C.

The theoretical isocyanate content of the reaction product is 29.09% and that of the diisocyanate of the formula (I) with n=2 is 12.68%; the value found was 20.3%.

Elemental analysis of the reaction product gave the following values, compared to the calculated values for $C_{22}H_{18}N_4O_5$(418.41) and for the dimer (n=2) $C_{35}H_{30}N_6O_8$ (662.67):

|  | C | H | N | O | P | Formula (I) |
|---|---|---|---|---|---|---|
| calculated | 63.15 | 4.34 | 13.39 | 19.12 | 0.0 | n = 1 |
| calculated | 63.44 | 4.56 | 12.68 | 19.32 | —/— | n = 2 |
| found | 62.6 | 4.6 | 13.8 | 19.1 | 0.062 | found |

Elemental analysis of the dimer gave, for $C_{24}H_{26}N_4O_7$ (482.50):

|  | C | H | N | O |
|---|---|---|---|---|
| calculated | 59.54 | 5.34 | 11.61 | 23.21 |
| found | 58.3 | 5.3 | 12.8 | 24.2 |

The $^1$H-NMR spectrum in $CDCl_3$ gave the following chemical shifts δ in ppm:

1.78 (s, 3H, Me), 2.18, 2.22 (2s, 6H, Ar—Me), 2.31 (s, 3H, CO-Me), 7.1 (mc, 6H, aromat. H).

The mass spectrum gave (EI): m/e=173 (96%), 220 (41%), 375 (100%), 418 (33%, M$^+$ of reaction product), 662 (<1%, M$^+$ of diisocyanate of the formula (I) with n=2).

2.1. 87.0 g (0.5 mol) of 2,4-TDI were dissolved in 300 ml of dry dichloromethane and reacted with 18.6 g (0.0357 mol) of 2,2,2-triphenoxy-4,5-diphenyl-2,2-dihydro–1,3,2-dioxaphospholene. The mixture was refluxed for 24 hours and the solvent was subsequently distilled off under atmospheric pressure. Excess 2,4-TDI and the reaction by-product triphenyl phosphate were distilled off at 2 mbar and 200° C. The distillation residue is the reaction product 5-benzyl-1,3-bis(3-isocyanato-4-methylphenyl)-5-phenylhydantoin and is a yellowish oil which gradually solidifies and has an isocyanate content of 17.3% (theoretically 16.9%).

Elemental analysis gave, for $C_{22}H_{18}N_4O_5$ (418.41):

|  | C | H | N | O |
|---|---|---|---|---|
| calculated | 74.7 | 4.67 | 11.8 | 10.1 |
| found | 69.6 | 4.4 | 7.0 | 17.6 |

2.2. The following reactions were carried out in an analogous way: 909 g of tolylene 2,4-/2,6-diisocyanate 80:20 were reacted with 95.0 g of 5 2,2,2-trimethoxy-4,5-dimethyl–2,2-dihydro-1,3,2-dioxaphospholene to give the corresponding hydantoin-modified diisocyanate which is a yellow oil that gradually solidifies and has an isocyanate content of 21.3% (theoretically 20.09%).

Elemental analysis gave, for $C_{22}H_{18}N_4O_5$ (418.41):

|  | C | H | N | O | P |
|---|---|---|---|---|---|
| calculated | 63.15 | 4.34 | 13.39 | 19.12 | 0.0 |
| found | 62.3 | 4.7 | 13.8 | 18.5 | 0.048 |

2.3. 87 g of tolylene 2,4-/2,6-diisocyanate 80:20 were reacted with 18.6 g of 2,2,2-triphenoxy-4,5-diphenyl-2, 2-dihydro-1,3,2-dioxaphospholene to give the corresponding hydantoin-modified diisocyanate, a yellow oil that gradually solidifies and has an isocyanate content of 15.3% (theoretically 16.9%).

2.4. 87 g of tolylene 2,4-/2,6-diisocyanate 65:35 were reacted with 18.6 g of 2,2,2-trimethoxy-4,5-dimethyl-2,2-dihydro-1,3,2-dioxaphospholene to give the corresponding hydantoin-modified diisocyanate. A yellowish, very viscous oil having an isocyanate content of 19.0% (theoretically 20.09%) is obtained.

Elemental analysis gave, for $C_{22}H_{18}N_4O_5$ (418.41):

|  | C | H | N | O | P |
|---|---|---|---|---|---|
| calculated | 63.15 | 4.34 | 13.39 | 19.12 | 0.0 |
| found | 62.7 | 4.2 | 14.4 | 19.2 | 0.06 |

3. 42.0 g (0.2 mol) of trimethoxy-4,5-dimethyl-2,2-dihydro-1,3,2-dioxaphospholene were added dropwise to a solution of 250 g (1.0 mol) of diphenylmethane 4,4'-diisocyanate (MDI) in 300 ml of dichloromethane at room temperature under protective gas. The mixture was refluxed for 24 hours. After cooling, the solvent was removed and excess MDI and trimethyl phosphate formed were removed at 3–4 mbar and 180–190° C. in a thin-film evaporator. The reaction product was obtained in a yield of 91 g (80%) as an oil which solidifies to give a solid having a melting point of 108° C. An isocyanate content of 11.5% was found (theoretically 14.7%).

The bisurethane of this product too was synthesized in the manner described under . . . ; the bisurethane has a melting point of 101–121° C.

Elemental analysis gave:

|  | C | H | O | N |
|---|---|---|---|---|
| calculated | 71.6 | 4.6 | 14.0 | 9.8 |
| found | 66.6 | 5.8 | 8.1 | 8.7 |

4. Diisocyanate I:

50.5 g (0.2 mol) of 2,2,2-triethoxy-4,5-dimethyl-2,2-dihydro-1,3,2-dioxaphospholene were added dropwise to a solution of 200 g (0.80 mol) of polymeric diphenylmethane 4,4'-diisocyanate (Polymeric MDI having a viscosity of 200 mPa·s at 25° C.) in 300 ml of dichloromethane at room temperature under protective gas. The mixture was refluxed for 24 hours. The mixture was subsequently cooled and the solvent was distilled off under atmospheric pressure. Without further distillation, an oil having an isocyanate content of 14.8% and a viscosity of 29 Pa·s (23° C.) was obtained. The oil further comprised the reaction by-product triethyl phosphate.

After distilling off the reaction by-product triethyl phosphate under reduced pressure in a thin-film evaporator, the product had an isocyanate content of 18.9% and a viscosity of 77 Pa·s (60° C.).

5. Diisocyanate 2:

50.5 g (0.2 mol) of 2,2,2-triethoxy-4,5-dimethyl-2,2-dihydro- 1,3,2-dioxaphospholene were added dropwise to a solution of 300.4 g (1.20 mol) of polymeric MDI (Cupranat M-20S) in 300 ml of dichloromethane at room temperature under protective gas. The reaction was carried out analogously to that for diisocyanate 1. An oil having an isocyanate content of 18.6% (19.1%) and a viscosity of 6Pa·s at 23° C. (0.170Pas at 60° C.) was obtained. After distilling off the reaction by-product triethyl phosphate under reduced pressure in a thin-film evaporator, the product had an isocyanate content of 21.6% (22.5%) and a viscosity of 3.87 Pa·s at 60° C. (5.51 (Pa·s at 60° C.).

6. Diisocyanate 3:

50.5 g (0.2 mol) of 2,2,2-triethoxy-4,5-dimethyl-2,2-dihydro-1,3,2-dioxaphospholene were added dropwise to a solution of 250 g (1.00 mol) of diphenylmethane 4,4'-diisocyanate (MDI) in 300 ml of dichloromethane at room temperature under protective gas. The reaction was carried out analogously to that for diisocyanate 1. An oil having an isocyanate content of 18.0% and a viscosity of 0.091 Pa·s (23° C.) was obtained. After distilling off some of the reaction by-product triethyl phosphate and excess 2,2,2-triethoxy-4,5-dimethyl-2,2-dihydro-1,3,2-dioxaphospholene under reduced pressure in a thin-film evaporator, the product had an isocyanate content of 20.8% and a viscosity of 0.69 Pa·s (23° C.).

7. Diisocyanate 4:

50.5g (0.2 mol) of 2,2,2-triethoxy-4,5-dimethyl-2,2-dihydro-1,3,2-dioxaphospholene were added dropwise to a solution of 200 g (0.80 mol) of MDI in 300 ml of dichloromethane at room temperature under protective gas. The reaction was carried out analogously to that for diisocyanate 1. An oil having an isocyanate content of 17.5% and a viscosity of 0.095 Pa·s at 23° C. (0.170 Pa·s at 60° C.) was obtained. After distilling off the reaction by-product triethyl phosphate under reduced pressure in a thin-film evaporator, the product had an isocyanate content of 21.1% and a viscosity of 0.7 Pa·s (23° C.).

8. Standard diisocyanate:

A mixture of diphenylmethane 4,4'-diisocyanate (MDI) and polymeric diphenylmethane 4,4'-diisocyanate (polymeric MDI) having an isocyanate content of 31.7% and a viscosity of 0.209 Pa·s (25° C.).

Diisocyanate mixture 1: 80:20 mixture of the standard diisocyanate and diisocyanate 1

Diisocyanate mixture 2: 80:20 mixture of the standard diisocyanate and diisocyanate 2

Diisocyanate mixture 3: 80:20 mixture of the standard diisocyanate and diisocyanate 3

Diisocyanate mixture 4: 80:20 mixture of the standard diisocyanate and diisocyanate 4

The mixtures described here are prepared using a mixing vessel with a blade stirrer.

III. Polyols

The amounts (parts) indicated below are by weight.

Polyol 1 (Lupranol® L 3422):

25.2 parts of sorbitol, 74.8 parts of propylene oxide, in the presence of KOH catalyst, and 0.5 parts of water. The hydroxyl number is 495 mg KOH/g, the viscosity is 17.9 Pa·s (20° C.) and the functionality is 5.

Polyol 2 (Lupranol® VP 9196):

1 part of sucrose, 1 part of pentaerythritol, 2 parts of diethylene glycol, propylene oxide, 0.5 parts of water and KOH as catalyst. The hydroxyl number is 400 mg KOH/g, and the viscosity is 2.2 Pa·s (20° C.). 20

Polyol 3 (Luprapheng 8004):

A polyester alcohol derived from adipic acid, phthalic anhydride and oleic acid in a ratio of 1:2:1 and 1,1,1-trimethylolpropane and having a number average molecular weight ($M_n$) of 530 g/mol. The hydroxyl number is 385 mg KOH/g and the viscosity is 1.37 Pa·s (70° C.).

Polyol 4 (Lupranol® 2045):

Glycerol, propylene oxide as first block and ethylene oxide as terminal block. The hydroxyl number is 35 mg KOH/g and the viscosity is 0.85 Pa·s (20° C.). The mass ratio of ethylene oxide to propylene oxide is 6.4.

IV. Rigid Polyurethane Foam

A molding was produced to test the rigid polyurethane foams.

672 g of a component A consisting of a mixture of
- 53.56 parts of polyol 1
- 28.04 parts of polyol 2
- 5.61 parts of dipropylene glycol
- 1.87 parts of glycerol
- 1.4 parts of polyethersiloxanes from TH Goldschmidt as stabilizer mixture
- 2.14 parts of a catalyst mixture of tertiary dimethylcyclohexylamine
- 0.84 parts of water
- 6.54 parts of cyclopentane and a component B corresponding to the diisocyanate to be examined were poured into a housing heated to 45° C. (mold; 300×400×80 mm) and the housing was subsequently closed tightly. The overall density of the molding was 70±1 kg/M$^3$. The time until removal from the mold was 30 minutes. After 24 hours, test specimens were sawn from the interior of the foam for measurement of the thermal conductivity and the heat distortion resistance.

The heat distortion resistance was measured as deformation in percent at 170° C. by the method of DIN standard 18164 on test specimens having dimensions of 50×50×50 mm after loading at 0.04 N/mm$^2$ for 24 hours.

In the individual formulations for the rigid polyurethane foams, the molar ratio of isocyanate groups to hydrogen-active groups was kept constant at 118 and the amount of isocyanate for the component B was varied:

Polyurethane 1: 100 parts of A+155 parts of diisocyanate mixture 1

Polyurethane 2: 100 parts of A+152 parts of diisocyanate mixture 2

Polyurethane 3: 100 parts of A+157 parts of diisocyanate mixture 3

Polyurethane 4: 100 parts of A+153 parts of diisocyanate mixture 4

The properties shown in Table 1 were obtained for the test specimens from the molding:

TABLE 1

| Polyurethane | 1 | 2 | 3 | 4 |
|---|---|---|---|---|
| Pot life [s] | 12 | 12 | 13 | 12 |
| Fiber time [s] | 64 | 64 | 63 | 61 |
| Rise time [s] | 102 | 100 | 99 | 94 |
| Free-foamed density [kg/m$^3$] | 51.7 | 55.7 | 51.1 | 56.9 |
| Overall density [kg/m$^3$] | 71 | 71 | 71 | 71 |
| Compressive strength [N/mm$^2$] | 0.59 | 0.59 | 0.49 | 0.49 |
| Thermal conductivity after 7d [mW/mK] | 24.9 | 24.7 | 24.6 | 23.6 |
| Heat distortion resistance at 170° C., in % | 11 | 12.2 | | 16.8 |

Rigid polyurethane/polyisocyanurate foams by foaming in a cup were produced from a component A:
- 25.6 parts of polyol 3
- 31.65 parts of polyol 4
- 16.6 parts of dipropylene glycol
- 2.58 parts of polyethersiloxanes from TH Goldschmidt as stabilizer mixture
- 2.71 parts of ethylene glycol
- 0.38 parts of water
- 2.41 parts of potassium acetate
- 0.27 parts of catalyst mixture of tertiary amines
- 17.8 parts of cyclopentane and component B corresponding to the diisocyanate to be examined. The components were both brought to 20±0.5° C. 78 g of the mixture were in each case stirred for 10 seconds at 1750 rpm, in a cardboard cup having a capacity of about 660 ml to give a foam. Using methods known to those skilled in the art, cream time, rise time and fiber time were measured on the rising foam and the density of the cured foam was measured.

In the individual formulations for the rigid polyurethane/polyisocyanurate foams, the molar ratio of isocyanate groups to hydroxyl groups was kept constant at 418 and the amount of isocyanate for the component B was varied:

Polyurethane 5: 100 parts of A+347 parts of diisocyanate mixture 1

Polyurethane 6: 100 parts of A+340 parts of diisocyanate mixture 2

Polyurethane 7: 100 parts of A+351 parts of diisocyanate mixture 3

Polyurethane 8: 100 parts of A+343 parts of diisocyanate mixture 4

The properties shown in Table 2 were found for the test specimens from foaming in a cup:

TABLE 2

| Polyurethane | 5 | 6 | 7 | 8 |
|---|---|---|---|---|
| Pot life [s] | 15 | 15 | 16 | 17 |
| Fiber time [s] | 30 | 29 | 33 | 33 |
| Rise time [s] | 51 | 45 | 51 | 50 |
| Free-foamed density [kg/m$^3$] | 51.9 | 56.6 | 51.6 | 53.5 |
| Heat distortion resistance at 200° C., in % | 10.1 | 6.8 | 25.0 | 17.2 |

V. Polyurethane Surface Coating Compositions

Hydantoin-containing hexamethylene 1,6-diisocyanate:

168 g of hexamethylene 1,6-diisocyanate (HDI) and 350 ml of dichloromethane were placed in a reaction vessel under protective gas. At room temperature, 18.6 g of 2,2,2-trimethoxy-4,5-dimethyl-2,2-dihydro-1,3,2-dioxaphospholene dissolved in 50 ml of dichloromethane were added slowly. The mixture was subsequently refluxed for 24 hours. After the solvent had been distilled off under atmospheric pressure, excess HDI and trimethyl phosphate formed were distilled off at 5 mbar and 150° C. The distillation residue (reaction product), namely 5-acetyl- 1,3-bis(6-isocyanatohexamethylene)-5-methylhydantoin, is a pale yellow liquid having a viscosity of 0.450 Pa·s (23° C.). The isocyanate content of the hydantoin-modified hexamethylene 1,6-diisocyanate is theoretically 20.7% and was determined experimentally as 17.5%.

The hydantoin-modified hexamethylene 1,6-diisocyanate was used in pigmented polyurethane surface coating compositions (pigment: TiO$_2$ Kronos® 2310 from Kronos Titan GmbH, Leverkusen) based on a hydroxyl-containing acrylate resin having a weight average molecular weight of about 6000 and an OH number of 135 (mg KOH/g of resin; Lumitol® H 136 from BASF) and an acrylate resin having a mean molecular weight of about 8000 and an OH number of 85 (Lumitol® H 85 from BASF).

For comparison, corresponding surface coating compositions were prepared using a low-viscosity aliphatic polyisocyanate based on HDI (isocyanurate type; Basonat® PLR 8900 from BASF) and having a comparable isocyanate content and a viscosity of 1.195 Pa·s (23° C.).

The surface coating compositions examined had the following compositions:

Surface coating composition 1: 100 parts of Lumitol® H 85, 56.36 parts of TiO$_2$ Kronos® 2310, 25.45 parts of n-butyl acetate/xylene (2:3) and 15.45 parts of hydantoin-modified hexamethylene 1,6-diisocyanate Surface coating composition 2: 100 parts of Lumitol® H 85, 56.36 parts of TiO$_2$ Kronos® 2310, 25.79 parts of n-butyl acetate/xylene (2:3) and 15.79 parts of Basonat® PLR 8900

Surface coating composition 3: 100 parts of Lumitol® H 136, 80.98 parts of TiO$_2$ Kronos® 2310, 71.22 parts of n-butyl acetate/xylene (2:3) and 31.22 parts of hydantoin-modified hexamethylene 1,6-diisocyanate Surface coating composition 4: 100 parts of Lumitol® H 136, 80.98 parts of TiO$_2$ Kronos® 2310, 71.93 parts of n-butyl acetate/xylene (2:3) and 31.93 parts of Basonat® PLR 8900

The surface coating compositions in which hexamethylene 1,6-diisocyanate containing hydantoin groups had been used displayed better elasticity compared to those prepared using the commercial polyisocyanate.

TABLE 3

| Surface coating composition | 1 | 2 | 3 | 4 |
|---|---|---|---|---|
| Erichsen indentation [mm] DIN 53156 | 8.9/9.2 | 7.1/7.5 | 7.3/7.9 | 7.0/7.1 |

The surface coating compositions 1–4 were applied by doctor blade to bonderized iron of the type 26/60-OC from Chemetall GmbH, Frankfurt. The wet film thickness was 150 μm.

We claim:

1. A diisocyanate of the formula (I)

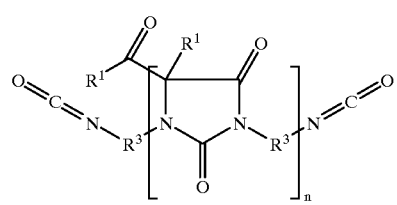

(I)

where $R^1$ is a $C_1$–$C_{10}$-hydrocarbon radical and $R^3$ is a $C_1$–$C_{12}$-hydrocarbon group and n is an integer from 1 to 10.

2. A diisocyanate of the formula (I) as claimed in claim 1, wherein $R^3$ is an alkylene group having from 3 to 12 carbon atoms, a cycloalkylene group having from 3 to 12 carbon atoms or an arylene group having from 7 to 12 carbon atoms.

3. A process for preparing diisocyanates of the formula (I)

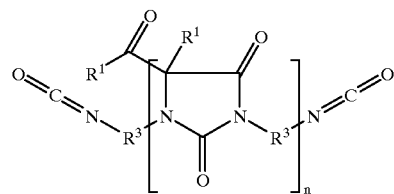

(I)

wherein $R^1$ is a $C_1$ to $C_{10}$ hydrocarbon radical, $R^3$ is a $C_1$ to $C_{12}$ hydrocarbon group, and n is an integer having a value of from 1 to 10, comprising the steps of:

a) providing at least one phospholene of the formula (II)

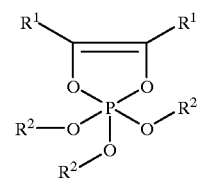

(II)

wherein $R^1$ is a $C_1$ to $C_{10}$ hydrocarbon radical and $R^2$ is a $C_1$ to $C_{10}$ hydrocarbon radical;

b) providing at least one diisocyanate of the formula (III)

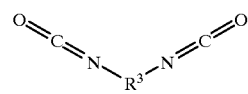

(III)

wherein $R^3$ is a $C_1$ to $C_{12}$ hydrocarbon group; and c) reacting the at least one phospholene of the formula (II) with the at least one diisocyanate of the formula (III) to form a diisocyanate of the formula (I) and a phosphate of the formula (IV)

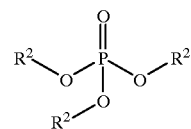

(IV)

wherein $R^2$ is a $C_1$ to $C_{10}$ hydrocarbon radical.

4. A process as recited in claim 3, comprising providing the at least one diisocyanate of the formula (III) in a molar excess compared to the at least one phospholene of the formula (II).

5. A composition obtained by a process as claimed in claim 4, comprising:

at least one diisocyanate of the formula (I)

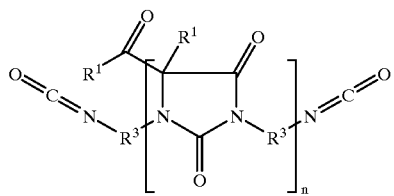
(I)

wherein $R^1$ is a $C_1$ to $C_{10}$ hydrocarbon radical, and $R^3$ is a $C_1$ to $C_{12}$ hydrocarbon group and n is an integer having a value of from 1 to 10; and at least one diisocyanate of the formula (III)

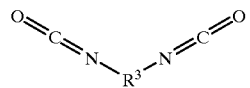
(III)

wherein $R^3$ is a $C_1$ to $C_{12}$ hydrocarbon group.

6. A process as claimed in claim 3, wherein the phosphate of the formula (IV) formed in the reaction is removed completely from the reaction mixture.

* * * * *